United States Patent

Matayabas, Jr. et al.

Patent Number: 5,536,882
Date of Patent: Jul. 16, 1996

[54] PREPARATION OF POLYETHER GLYCOLS AND ALCOHOLS BY THE POLYMERIZATION 3,4-EPOXY-1-BUTENE

[75] Inventors: James C. Matayabas, Jr.; Stephen N. Falling, both of Kingsport, Tenn.

[73] Assignee: Eastman Chemical Company, Kingsport, Tenn.

[21] Appl. No.: 398,245

[22] Filed: Mar. 3, 1995

Related U.S. Application Data

[62] Division of Ser. No. 181,736, Jan. 18, 1994, Pat. No. 5,434,314.

[51] Int. Cl.$^6$ .................................. C07C 41/06
[52] U.S. Cl. .................. 568/616; 568/650; 568/651; 568/670; 568/675; 536/120
[58] Field of Search ............................ 568/675, 616, 568/650, 651, 670; 536/120

[56] References Cited

U.S. PATENT DOCUMENTS

| | | |
|---|---|---|
| 3,133,905 | 5/1964 | Suyder et al. |
| 3,509,118 | 4/1970 | Vandenberg et al. |
| 5,434,314 | 7/1995 | Matayabas et al. ............... 568/616 |

OTHER PUBLICATIONS

Bartlett, *J. Am. Chem. Soc.*, 70, 926 (1948).
Ivanchev, *J. Polym. Sci., Polym. Chem. Ed.*, 18, 2051–2059.
Tsuruta, *Macromol. Chem.*, 111, 236–246 (1968).
Kubisa, *Makromol. Chem., Macromol Symp.*, 13/14, 203 (1988).
Brezezinska, *Makromol. Chem., Rapid Commun.*, 7, 1 (1986).
Bednarek, *Makromol. Chem.*, Suppl., 15, 49 (1989).
Biedron, *Makromol. Chem., Macromol Symp.*, 32, 155 (1990).

*Primary Examiner*—Johann Richter
*Assistant Examiner*—John Peabody
*Attorney, Agent, or Firm*—J. Frederick Thomsen; Harry J. Gwinnell

[57] ABSTRACT

Disclosed are novel polyether compounds obtained by the reaction or polymerization of 3,4-epoxy-1-butene in the presence of an acidic catalyst and a nucleophilic initiator compound. The polyether compounds comprise n units of residue (1) and m units of residue (2), wherein the total value of n+m is 2 to 70, n/(n+m) is a value in the range of 0.70 to 0.95, and residues (1) and (2) have the structures:

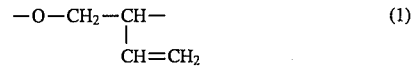

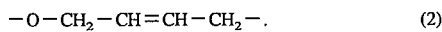

5 Claims, No Drawings

PREPARATION OF POLYETHER GLYCOLS AND ALCOHOLS BY THE POLYMERIZATION 3,4-EPOXY-1-BUTENE

This is a divisional application of application Ser. No. 08/181,736, filed Jan. 18, 1994, now U.S. Pat. No. 5,434,314.

This invention pertains to certain novel polyether compounds. More specifically, this invention pertains to polyether glycols and alcohols containing repeating units of the structure:

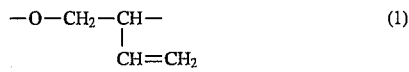

and

This invention also pertains to a process for the preparation of the polyether compounds by the polymerization of 3,4-epoxy-1-butene in the presence of an acidic catalyst and a hydroxyl initiator compound.

P. D. Bartlett et al., J. Am. Chem. Soc., 70, 926 (1948), disclose the sulfuric acid-catalyzed methanolysis of 3,4-epoxy-1-butene to give 1-hydroxy-2-methoxy-3-butene. A. M. Ross, et al., J. Am. Chem. Soc., 104, 1658 (1982), disclose the acid-catalyzed hydrolysis of 3,4-epoxy-1-butene to produce a mixture of 3,4-dihydroxy-1-butene and 1,4-dihydroxy-2-butene in a 96/4 ratio. Polymers comprising residues (1) and (2) are not contemplated by the above-cited prior art, and the reactions exemplified employ an excess of the nucleophile.

The polymerization and copolymerization of 3,4-epoxy-1-butene is known. U.S. Pat. No. 2,680,109 discloses the polymerization of unsaturated 1, 2-epoxides, including 3,4-epoxy-1-butene, in the presence of stannic chloride and a small amount of water.

British Patent 869,112 and U.S. Pat. Nos. 3,031,439 and 3,417,064 disclose the copolymerization of 3,4-epoxy-1-butene with ethylene oxide and propylene oxide, using as catalyst strontium carbonate containing a small amount of water.

U.S. Pat. Nos. 3,158,705, 3,158,581, and 3,158,591 disclose the polymerization of 3,4-epoxy-1-butene to give polyethers consisting only of residue (1), using as catalyst trialkylaluminum compounds prereacted with water. These patents also disclose the copolymerization of 3,4-epoxy-1-butene with ethylene oxide, propylene oxide, and epichlorohydrin, using as catalyst trialkylaluminum compounds prereacted with water. U.S. Pat. No. 3,509,118 discloses the preparation of unsaturated polyether glycols containing only residue (1) prepared by n-butyl lithium cleavage of the high molecular weight polyethers prepared by the polymerization of 3,4-epoxy-1-butene in benzene using triethylaluminum prereacted with water.

U.S. Pat. No. 3,133,905 discloses the copolymerization of a small amount of 3,4-epoxy-1-butene with ethylene oxide using ethylene glycol as the initiator and solid sodium hydroxide as the catalyst in a pressurized resin pot. U.S. Pat. No. 3,133,905 also discloses the copolymerization of small amounts of 3,4-epoxy-1-butene with tetrahydrofuran using as catalyst boron trifluoride; however, only about two-thirds of the available 3,4-epoxy-1-butene is incorporated into the copolyether, and the repeat-unit structure is not disclosed. S. S. Ivanchev, et al., J. Polym. Sci., Polym. Chem. Ed., 18, 2051–2059 (1980), investigated the homopolymerization of 3,4-epoxy-1-butene with boron trifluoride etherate and disclose that the rate of termination is much faster than the rate of propagation, leaving much of the 3,4-epoxy-1-butene unreacted. Our investigation of this chemistry corroborates this result, i.e., low yields of a thermally-unstable, white material are obtained and the chloroform-soluble portion of the material contains only residue (1). U.S. Pat. No. 3,468,847 discloses the copolymerization of 3,4-epoxy-1-butene, hexafluoroacetone, ethylene oxide, and propylene oxide, using cesium fluoride as catalyst.

Tsuruta, et al., Macromol. Chem., 111, 236–246 (1968), disclose that diethylzinc prereacted with water polymerizes 3,4-epoxy-1-butene to give a 54% yield of high molecular weight polyether containing only residue (1). Tsuruta, et al., also disclose the isolation of a 3% yield of polyether from 3,4-epoxy-1-butene and uncomplexed diethylzinc as catalyst having evidence of internal double bonds [residue (2)] by infrared spectroscopy. Our investigation of this chemistry resulted in no isolable polymer.

U.S. Pat. No. 2,570,601 discloses the thermally induced polymerization of 3,4-epoxy-1-butene to a hard yellow resin and a small amount of a viscous yellow oil. U.S. Pat. No. 2,570,601 also discloses the thermally induced copolymerization of 3,4-epoxy-1-butene and α-methylstyrene to a brittle, clear, amber thermoplastic resin. U.S. Pat. No. 2,582,708 discloses radically initiated copolymerization of 3,4-epoxy-1-butene and maleic anhydride. U.S. Pat. No. 2,720,530 discloses residues of unsaturated polyether containing only residue (2) formed by vinyl polymerization of 3,4-epoxy-1-butene initiated by excess n-butyraldehyde and benzoyl peroxide. U.S. Pat. Nos. 5,013,806, 5,071,930, and 5,071,931 disclose the preparation of alternating copolymers from 3,4-epoxy-1-butene and maleic anhydride by radical initiation, wherein the copolymers comprise residues (1) and (2) alternating with the maleic anhydride derived diradical.

A series of papers [P. Kubisa, Makromol. Chem., Macromol Symp., 13/14, 203 (1988); K. Brzezinska, et al., Makromol. Chem., Rapid Commun., 7, 1 (1986); M. Bednarek, et al., Makromol. Chem., Suppl., 15, 49 (1989); T. Biedron, et al., Makromol. Chem., Macromol Symp., 32, 155 (1990)] teaches that cationic polymerization of oxiranes in the presence of alcohols proceeds by an activated monomer mechanism in which the propagation proceeds by the addition of protonated monomer to the hydroxyl-terminated growing macromolecule. This process has been shown to be useful for the polymerization of ethylene oxide, propylene oxide, and epichlorohydrin, having good molecular weight control and reduced formation of cyclic oligomers. These papers disclose that when propylene oxide is polymerized under these conditions, the resulting polyether glycol contains both primary and secondary hydroxyl end groups in a ratio of 45 to 55, respectively. These papers do not suggest that the application of the disclosed conditions of activated monomer polymerization to 3,4-epoxy-1-butene would result in a copolymer having mostly (if not completely) primary hydroxyl end groups and containing both residues (1) and (2).

None of the prior art discloses our novel polyether compounds described in more detail hereinbelow or a process whereby the novel polyether compounds may be obtained. The polyether compounds provided by the present invention are comprised of n units of residue (1) and m units of residue (2), wherein the total value of n+m is 2 to 70, n/(n+m) is a value in the range of 0.70 to 0.95, i.e., residue (1) constitutes from 70 to 95 mole percent of the total moles of residues (1) and (2), and residues (1) and (2) have the structures

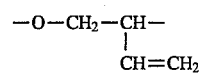

The polyether compounds may be used in the preparation or formulation of surfactants and other compositions analogous to compositions derived from known polyether polymers.

The process utilized to prepare the above-described polyether compounds is believed to be novel and comprises polymerizing 3,4-epoxy-1-butene in the presence of a catalytic amount of certain acidic compounds and a hydroxyl initiator compound to obtain the polyether compounds described in the preceding paragraph. The initiator compound may be selected from various nucleophiles such as the hydroxyl compounds disclosed in Published International PCT Application WO 89/02883. The initiator compound preferably is selected from various organic hydroxyl compounds such as alcohols, polyols, i.e., polyhydroxyl compounds containing 2 to 6 hydroxyl groups, and hydroxyl-terminated polymers such as hydroxyl-terminated polyether and polyester polymers. When an alcohol is used as the initiator, the polymeric product obtained has a hydroxyl group on one end of the chain (a terminal hydroxyl group) and thus is a polymeric alcohol. The other end of the polymer chain is terminated with the residue of the alcohol initiator, e.g., a residue having the formula —O—$R^1$ wherein $R^1$ is the residue of an alcohol, preferably an alkyl group, containing up to about 20 carbon atoms. When a polyhydroxyl compound is used as the initiator, the polymer grows from at least 2 of the hydroxyl groups of the initiator, and the subsequently-obtained polymer is a polyhydroxyl polymer. The residue of the polyhydroxy initiators may be represented by the formula —O—$R^2$—O— wherein $R^2$ is the residue of a polyhydroxy initiator.

Suitable alcohols include low molecular weight organic alcohols and polymeric alcohols which may be linear or branched-chain aliphatic, alicyclic or aromatic. Although secondary or tertiary alcohols may be used, primary alcohols are preferred. Some typically useful alcohol initiators include methyl alcohol, ethyl alcohol, n-butyl alcohol, isobutyl alcohol, 2-ethylhexyl alcohol, n-decyl alcohol, stearyl alcohol, cetyl alcohol, allyl alcohol, benzyl alcohol, phenol, cresol, and the like. Typically useful glycol initiators include ethylene glycol, 1,2-propanediol, 1,3-propanediol, 1,2-butanediol, 1,4-butanediol, 1,6-hexanediol, 1,4-cyclohexanediol, 1,4-cyclohexanedimethanol, 2,2-dimethyl-1,3-propanediol, 2,2,4-trimethyl-1,3-pentanediol, 2,2,4,4-tetramethyl-1,3-cyclobutanediol, 1,4-dihydroxy-2-butene, 3,4-dihydroxy-1-butene, benzenediols such as hydroquinone and resorcinol, and the like. Typically useful polymeric alcohols and glycols include polyethylene glycol, polyethylene glycol monomethyl ether, polypropylene glycol, polypropylene glycol monobutyl ether, poly(tetramethylene ether) glycol, and the like. Low molecular weight hydroxyl-terminated polyesters also may function as the hydroxyl initiator compound. Typically useful polyols include glycerol, starch, sucrose, glucose, pentaerythritol, and the like. Water also may be used as the initiator. Diols having 2 to 6 carbon atoms constitute the preferred initiators, i.e., wherein $R^2$ is alkylene of 2 to 6 carbon atoms. The acidic catalysts which may be used in the process of the present invention are selected from strong acids such as sulfuric acid; perchloric acid; fluoroboric acid; strongly acidic ion exchange resins, e.g., Amberlyst resins; and fluorosulfonic acids such as perfluoroalkanesulfonic acids containing up to about 6 carbon atoms, e.g., trifluoromethanesulfonic acid, fluorosulfonic acid, and perfluorosulfonic acid polymers, e.g., Nafion resins. Although strong acids generally are capable of effecting reaction of 3,4-epoxy-1-butene and an initiator, most exhibit limited activity and result in the formation of low molecular weight products. The most effective and, therefore, the preferred catalysts are the perfluoroalkanesulfonic acids such as trifluoromethanesulfonic acid and, especially, Nafion NR-50 perfluorosulfonic acidic resin which has been cryogenically ground to 60 to 100 mesh (particles having an average diameter of 170 to 250 microns), available from C.G. Processing of Rockland, Del. The amount of the acidic catalyst which may be used can vary substantially depending, for example, on process conditions and the particular strong acid employed. In batch operation of the process, the amount of catalyst used typically is in the range of 0.5 to 1.5 mole percent based on the equivalents of initiator.

The polymerization reaction preferably is conducted in the presence of a solvent, e.g., an inert, organic solvent such as a hydrocarbon, chlorinated hydrocarbon, and the like. Specific examples of such solvents include benzene, toluene, xylene, heptane, methylene chloride, chloroform, and the like.

The process of the present invention may be carried out at temperatures in the range of about 0° to 150° C., depending upon the choice of initiator, solvent, and catalyst. Temperatures of about 20° to 60° C. are preferred. Reaction pressure is not an important part of our novel process and, therefore, the process typically is performed at approximately atmospheric pressure although pressure moderately above or below atmospheric may be used.

In the operation of our novel process, the primary reactant, 3,4-epoxy-1-butene, is added to a mixture of the acidic catalyst, the nucleophilic initiator compound, and any solvent used. The 3,4-epoxy-1-butene may be added all at once or, preferably, slowly or in stepwise increments to a mixture of the catalyst and the initiator. Stepwise addition of the 3,4-epoxy-1-butene monomer gives stepwise increase in polymer molecular weight; thus, molecular weight control is readily achieved by the stoichiometry of monomer to initiator. A wide variety of molecular weights may be achieved, but the molecular weights are generally controlled to provide polymers with molecular weights of about 500 to 3000 for use as condensation polymer intermediates. Slow addition of 3,4-epoxy-1-butene is preferred for controlling the heat of reaction, controlling the product molecular weight and molecular weight distribution, and minimizing side reactions. The polymerization reaction generally is rather rapid, and reaction usually is complete immediately after addition of the 3,4-epoxy-1-butene or up to about 16 hours after the completion of the addition, depending upon the rate of 3,4-epoxy-1-butene addition, temperature, and catalyst activity.

It is apparent from the above process description that the polyether polymers of the present invention can comprise, in addition to the 3,4-epoxy-1-butene residues, a minor or major amount of the residue of a nucleophilic initiator compound. For example, if a polymeric initiator, e.g., a hydroxyl-terminated polyoxyalkylene polymer, is employed and the number of repeat units of 3,4-epoxy-1-butene residues is relatively low, the 3,4-epoxy-1-butene residue content of the polymer may be less than 10 weight percent. On the other hand, if the initiator employed is a low molecular weight compound such as methanol, ethylene glycol, or water, the 3,4-epoxy-1-butene residues may constitute greater than 99 weight percent of the polymer. The polymers typically comprise at least 80 weight percent, preferably at least 90 weight percent, 3,4-epoxy-1-butene residues. Residues of the initiator compound typically constitute at least 1 weight percent (at least 0.5 weight percent when water is the initiator) of the total weight of the polyether polymers.

Our novel polyether polymers preferably are comprised of n units of residue (1) and m units of residue (2), wherein the total value of n+m is about 7 to 50, and n/(n+m) is a value in the range of 0.70 to 0.95. The polymers are further characterized in that at least 95% of the terminal hydroxyl groups are primary (rather than secondary) hydroxyl groups. NMR analyses of the polyethers of the present invention have failed to detect any secondary, terminal hydroxyl groups. The primary hydroxyl groups (and thus the polymers) are more reactive for condensation polymerizations reactions in general. The polyether polymers normally have a polydispersity value of less than 4, preferably in the range of 1 to 2.5. The polyether polymers wherein the total value of n+m is about 10 to 30 are particularly preferred. The preferred polyethers contain from about 5 to 20 weight percent, based on the weight of the polyether polymer, of hydroxyl initiator residues, preferably residues having the formula —O—$R^2$—O— wherein $R^2$ is alkylene of 2 to 6 carbon atoms.

The preparation of the novel polyether polymers of the present invention and the operation of the process are further illustrated by the following examples. NMR spectra are obtained on 300 or 400 MHz NMR spectrometers with samples dissolved in deuterated chloroform containing tetramethylsilane as an internal standard or deuterated acetone. The value of n/(n+m) is determined by comparison of the integrated proton NMR absorptions of residues (1) and residues (2), i.e.,

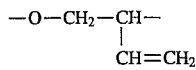
(1)

and

(2)

and all reported values relate only to the 3,4-epoxy-1-butene monomer units added and are, therefore, exclusive of the initiator fragment.

Absolute molecular weight distributions are determined by size-exclusion chromatography (SEC) with viscometry detection in tetrahydrofuran using four 10 μm PLgel mixed-bed columns. Absolute molecular weights are calculated from the viscosity data and a universal calibration curve constructed from narrow molecular weight distribution polystyrene standards. The value of n+m is determined from the SEC-determined number average molecular weight. Hydroxyl numbers are determined from titration of the acetic acid formed by the reaction of sample with acetic anhydride.

EXAMPLE 1

Methylene chloride (80 mL), 1,4-butanediol (3.62 g, 40.0 mmole), and 3 drops of trifluoromethane sulfonic acid are charged to a 3-neck, 300-mL, round-bottom flask having an argon atmosphere and equipped with a thermocouple, mechanical stirrer, and a septum with argon inlet. Stirring is begun and the reaction flask is cooled with a cooling bath composed of water and ice and having a temperature of 0° to 5° C. 3,4-Epoxy-1-butene (40 mL, 500 mmole) is added dropwise at a rate of 9 mL/hour by syringe pump. After the addition of the 3,4-epoxy-1-butene is complete, the cooling bath is removed and the reaction solution is allowed to warm to room temperature. Solid calcium oxide (about 1 g) is added and the mixture stirred for several hours to neutralize the acid. The mixture is then filtered and the filtrate evaporated to give 35 g of a clear, colorless oil having a n+m value of approximately 17 and a n/(n+m) value of 0.85; Mn=1270 and Mw/Mn=1.94; and hydroxyl number=100.5.

EXAMPLE 2

The procedure described in Example 1 is repeated in the absence of a solvent and at a reaction temperature between 20° and 30° C. by cooling with cool water and adding small amounts of ice as needed. The resulting clear, colorless oil has a n+m value of approximately 18 and a n/(n+m) value of 0.86; Mn=1305 and Mw/Mn=2.00; and hydroxyl number=97.18. NMR analysis of this product shows no evidence of secondary hydroxyl groups.

EXAMPLE 3

1,4-Butanediol (21.6 g, 0.240 mole) and 10 drops of trifluoromethane sulfonic acid dissolved in 250 mL of methylene chloride are charged to a 3-neck, 1-L, round-bottom flask having an argon atmosphere and equipped with a thermocouple, mechanical stirrer, septum, and reflux condenser with argon inlet. With stirring, 3,4-epoxy-1-butene (471 g, 6.72 mole) is added dropwise at a rate of 60 g/hour by liquid pump. The temperature rises initially to about 42° C., gently refluxing the solvent, and continued to rise, reaching 58° C. near the completion of the addition of the 3,4-epoxy-1-butene. After complete addition, the reaction solution is allowed to cool and stir for 1 hour. The reaction mixture is washed twice with water, dried over anhydrous magnesium sulfate, filtered, and evaporated to give 468 g of a light yellow oil having a n+m value of approximately 29 and a n/(n+m) value of about 0.83; Mn=2100 and Mw/Mn=2.64; and hydroxyl number=46.09.

EXAMPLE 4

1,4-Butanediol (0.90 g, 0,010 mole) and 1 drop of trifluoromethane sulfonic acid dissolved in 10 ml of toluene are charged to a reaction flask having a nitrogen atmosphere and equipped with a refluxing condenser. With stirring, the reaction solution is heated to 100° C. by an oil bath. 3,4-Epoxy-1-butene (9.1 g, 0.13 mole) is added dropwise at a rate of 0.15 mL/minute by syringe pump. After complete addition, the reaction solution is allowed to cool and stir for 15 minutes. The reaction mixture is washed twice with water, dried over anhydrous magnesium sulfate, filtered, and evaporated to give 8.0 g of a black oil having a n+m value of approximately 14 and a n/(n+m) value of about 0.74; Mn=950 and Mw/Mn=2.16; and hydroxyl number=95.0.

EXAMPLE 5

3,4-Dihydroxy-1-butene (0.88 g, 0,010 mole) and 1 drop of trifluoromethane sulfonic acid dissolved in 10 mL of methylene chloride are charged to a reaction flask having a nitrogen atmosphere and an 18° C. chilled water cooling bath. With stirring, 3,4-epoxy-1-butene (9.1 g, 0.13 mole) is added dropwise at a rate of 0.15 mL/minute by syringe pump. After complete addition, the reaction solution is allowed to cool and stir for 15 minute. The reaction mixture is washed with 5% sodium carbonate in water, dried over anhydrous sodium carbonate, filtered, and evaporated to give 8.6 g of a clear, colorless oil having a n+m value of approximately 14 and a n/(n+m) value of about 0.87; Mn=1400; and Mw/Mn=1.68. J-resolved NMR and $^{13}$C NMR analyses of this polyether product shows that essentially all of the terminal hydroxyl groups are primary hydroxyls since no secondary hydroxyl groups are detected.

EXAMPLE 6

The procedure described in Example 5 is repeated using 0.18 g (0.010 mole) of water as the initiator in place of 1,4-butanediol, yielding 8.6 g of a clear, colorless oil having a n+m value of approximately 15 and a n/(n+m) value of about 0.86; Mn=1320; and Mw/Mn=1.51. J-resolved NMR and $^{13}$C NMR analyses of this polyether product shows that essentially all of the terminal hydroxyl groups are primary hydroxyls since no secondary hydroxyl groups are detected.

The invention has been described in detail with particular reference to preferred embodiments thereof, but it will be understood that variations and modifications will be effected within the spirit and scope of the invention.

We claim:

1. Process for the preparation of a polyether polymer comprising n units of residue (1) and m units of residue (2), wherein the total value of n+m is 2 to 70, n/(n+m) is a value in the range of 0.70 to 0.95, and residues (1) and (2) have the structures:

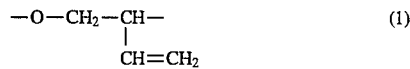
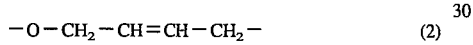

which comprises polymerizing 3,4-epoxy-1-butene in the presence of a catalytic amount of an acidic catalyst and a nucleophilic initiator compound.

2. The process of claim 1 wherein the acidic catalyst is a perfluoroalkanesulfonic acid having up to about 6 carbon atoms and the process is carried out at a temperature of about 0° to 100° C.

3. Process for the preparation of a polyether polymer comprising n units of residue (1) and m units of residue (2), wherein the total value of n+m is 7 to 50, n/(n+m) is a value in the range of 0.70 to 0.95, and residues (1) and (2) have the structures:

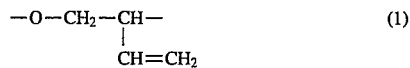

which comprises polymerizing 3,4-epoxy-1-butene at 20° to 60° C. in the presence of (i) a catalytic amount of trifluoromethanesulfonic acid or a perfluorosulfonic acidic resin and (ii) water or an organic hydroxyl initiator compound.

4. The process of claim 3 wherein 3,4-epoxy-1-butene is added slowly or in increments to a mixture of the trifluoromethanesulfonic acid, a glycol containing 2 to 6 carbon atoms and an inert, organic solvent.

5. Process for the preparation of a polyether polymer comprising n units of residue (1) and m units of residue (2), wherein the total value of n+m is 7 to 50, n/(n+m) is a value in the range of 0.70 to 0.95, and residues (1) and (2) have the structures:

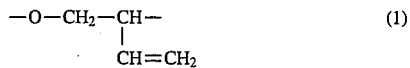
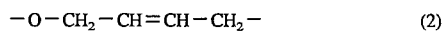

which comprises polymerizing 3,4-epoxy-1-butene at 20° to 60° C. in the presence of (i) a catalytic amount of trifluoromethanesulfonic acid or a perfluorosulfonic acidic resin and (ii) water or a glycol containing 2 to 6 carbon atoms.

* * * * *